United States Patent
Garcia-Olmo et al.

(10) Patent No.: US 11,253,632 B2
(45) Date of Patent: *Feb. 22, 2022

(54) BIOMATERIAL FOR SUTURING

(71) Applicants: TIGENIX, S.A.U., Madrid (ES); Universidad Autonoma de Madrid, Madrid (ES)

(72) Inventors: Damian Garcia-Olmo, Madrid (ES); Gema Fernandez Miguel, Madrid (ES); Manuel A. Gonzalez De La Pena, Madrid (ES); Mariano G. Arranz, Madrid (ES)

(73) Assignees: TIGENIX, S.A.U., Madrid (ES); Universidad Autonoma de Madrid, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/436,578

(22) Filed: Jun. 10, 2019

(65) Prior Publication Data

US 2020/0101199 A1 Apr. 2, 2020

Related U.S. Application Data

(63) Continuation of application No. 12/533,875, filed on Jul. 31, 2009, now abandoned, which is a
(Continued)

(30) Foreign Application Priority Data

Aug. 25, 2004 (ES) .................................. 200402083

(51) Int. Cl.
*A61L 27/38* (2006.01)
*A61L 17/14* (2006.01)
(Continued)

(52) U.S. Cl.
CPC ......... *A61L 27/3804* (2013.01); *A61L 17/145* (2013.01); *A61L 27/3839* (2013.01); *A61L 17/00* (2013.01); *C12N 5/0667* (2013.01)

(58) Field of Classification Search
CPC ............. A61L 27/3839; A61L 27/3804; A61L 17/145; A61L 17/00; C12N 5/0667
See application file for complete search history.

(56) References Cited

U.S. PATENT DOCUMENTS

| 3,842,439 A | 10/1974 | Connelly et al. |
| 4,409,974 A | 10/1983 | Freedland |

(Continued)

FOREIGN PATENT DOCUMENTS

| WO | WO-0267867 | 9/2002 |
| WO | WO-2005062857 | 7/2005 |

OTHER PUBLICATIONS

Miklos et al. Levatorplasty Release and Reconstruction of Rectovaginal Septum using Allogenic Dermal Graftinternational Urogynecology Journal (1999), 10, 405-406. (Year: 1999).*
(Continued)

*Primary Examiner* — Sean C. Barron
(74) *Attorney, Agent, or Firm* — Foley Hoag LLP

(57) ABSTRACT

A biomaterial for suturing comprising a physiologically compatible support material coated with a cellular population with proliferative and/or differentiation capacity, characteristics which facilitate the regeneration of the sutured tissue. This biomaterial for suturing not only brings together the two edges of an open wound, but also contributes actively to the healing process, thereby accelerating the tissue repair process. Also disclosed are methods for making the biomaterial and methods for using the biomaterials in therapy.

6 Claims, 5 Drawing Sheets

Related U.S. Application Data continuation of application No. 11/056,241, filed on Feb. 14, 2005, now abandoned.

(51) Int. Cl.
*C12N 5/0775* (2010.01)
*A61L 17/00* (2006.01)

(56) References Cited

U.S. PATENT DOCUMENTS

| | | | |
|---|---|---|---|
| 4,482,516 | A | 11/1984 | Bowman et al. |
| 5,236,563 | A | 8/1993 | Loh |
| 5,855,619 | A | 1/1999 | Caplan et al. |
| 6,004,341 | A | 12/1999 | Zhu et al. |
| 6,090,910 | A | 7/2000 | Shinoda et al. |
| 6,174,333 | B1 | 1/2001 | Kadiyala et al. |
| 6,264,675 | B1 | 7/2001 | Brotz |
| 6,835,377 | B2 | 12/2004 | Goldberg et al. |
| 2004/0166096 | A1 | 8/2004 | Kolkin et al. |

OTHER PUBLICATIONS

Georgiev-Hristov et al. Sutures enriched with adipose-derived stem cells decrease the local acute inflammation after tracheal anastomosis in a murine model. European Journal of Cardio-Thoracic Surgery 42 (2012) e40-e47. (Year: 2012).*
Aronson, S. B. et al., "Toxicity of the Cyanoacrylates", *Arch. Opthal.*, 84:342-349 (Sep. 1970).
Asencio A.F., et al., "Aproximación a los métodos de estudio de las anastomosis intestinales experimentales. I. Métodos bioquimicos, físicos y microangiográficos," *Cir. Esp.*, 46:805-810 (1989)(abstract in English).
Awad, Hani A., et al.; "Repair of patellar tendon injuries using a cell-collagen composite"; *J. Orthopaedic Research*, (2003) 21:420-431.
Awad, Hani A.,et. al.; "Chondrogenic differentiation of adipose-derived adult stem cells in agarose, alginate, and gelatin scaffolds"; *Biomaterials*, 25:3211-3222.
Beresford, J. N. et al .. "Evidence for an inverse relationship between the differentiation of adipocytic and osteogenic cells in rat marrow stromal cell cultures", *Journ. of Cell Science*, 102:341-351 (1992).
Brittberg, M., et al. "Treatment of deep cartilate defects in the knee with autologous chondrocyte transplantation," N. Engl. J. Med, 331: 889-895 (1994).
Caplan. A. I., "Mesenchymal Stem Cells," *Journal of Orthopedic Research*, 9:641-650 (1991).
De Ugarte, D. A. et al., "Comparison of Multi-Lineage Cells from Human Adipose Tissue and Bone Marrow," Cells Tissues Organs, 174:101-109 (2003).

Ellis, H., "The Aetiology of Post-Operative Abdominal Adhesions. An Experimental Study," *Br. J. Surg.*, 50:10-16 (1962).
European Search Report for EP 04380271.
Friedenstein, A J., "Precursor cells of mechanocytes", *Int. Rev. Cytol.*, 47:327-59 (1976).
Garcia-Olmo, D., et al.; "Autologous stem cell transplantation for treatment of rectovaginal fistula in perianal Crohn's disease: a new cell-based therapy"; *International Journal of Colorectal Disease*; 18:451-454.
Gimble, Jeffrey M., et al.; "Differentiation Potential of Adipose Derived Adult Stem (ADAS) Cells"; *Current Topics in Developmental Biology*; pp. 137-160.
Gimble, Jeffrey M.; "Adipose tissue-derived therapeutics"; *Expert Opin. Biol. Ther.* (2003). 3(5): pp. 705-713.
Haynesworth, S.E. et al., "Characterization of Cells with Osteogenic Potential from Human Marrow," *Bone*, 13:81-88 (1992).
International Search Report for PCT/ES2005/000468.
Johnstone, B. et al., "In Vitro Chondrogenesis of Bone Marrow-Derived Mesenchymal Progenitor Cells", *Exp. Cell* Res., 238:265-272 (1998).
Kim, Dong-Ik, et al.; "Comparative Study of Seeding and Culture Methods to Vascular Smooth Muscle Cells on Biodegradable Scaffold"; *J. Microbiol. Biotechnol.* (2004), 14(4), pp. 707-714.
Milde, L. N., M.D., "An Anaphylactic Reaction to Fibrin Glue", *Anesth. Ana/g.*, 69:684-686 (1989).
Pittenger, M. F., et al., "Multilineage Potential of Adult Human Mesenchymal Stem Cells", *Science*, 284(5411):143-147 (Apr. 2, 1999).
Ravo, B., "Colorectal Anastomotic Healing and Intracolonic Bypass Procedure", *Surg. Clin. North Am.*, 68:1267-1294 (1988).
Van Eijk, et al., "Tissue Engineering of Ligaments: A Comparison of Bone Marrow Stromal Cells, Anterior Cruciate Ligament, and Skin Fibroblasts as Cell Source"' *Tissue Engineering*, (2004) 10:893-903.
Verreet, P. R. et al., "Preventing Recurrent Postoperative Adhesions: An Experimental Study in Rats", *Eur. Surg. Res.*, 21:267-273 (1989).
Wakitani, S. et al., "Myogenic Cells Derived from Rat Bone Marrow Mesenchymal Stem Cells Exposed to 5-Azacytidine", *Muscle & Nerve*, 18(12):1417-1426 (Dec. 1995).
Young, Randell G., et al.; "Use of Mesenchymal Stem Cells in a Collagen Matrix for Achilles Tendon Repair"; J. Orthopedic Research; 16:406-413 (1998).
Zarapico, R. M. et al., "La asociación fibrino-desoxiribonnucleasa en la profilaxis de la adherencias peritoneales postoperativas", *Rev. Fac. Med.* Sevilla, 20:347-362 (1972)(abstract in English).
Zuk, P. A. et al., "Multilineage Cells from Human Adipose Tissue: Implications for Cell-Based Therapies", *Tissue Eng.*, 7(2):211-228 (Apr. 2001).
Zuk. P. A. et al., "Human Adipose Tissue Is a Source of Multipotent Stem Cells", *Mol. Biol. Cell*, 13(12):4279-4295 (Dec. 2002).

* cited by examiner

FIG. 4A 7mm
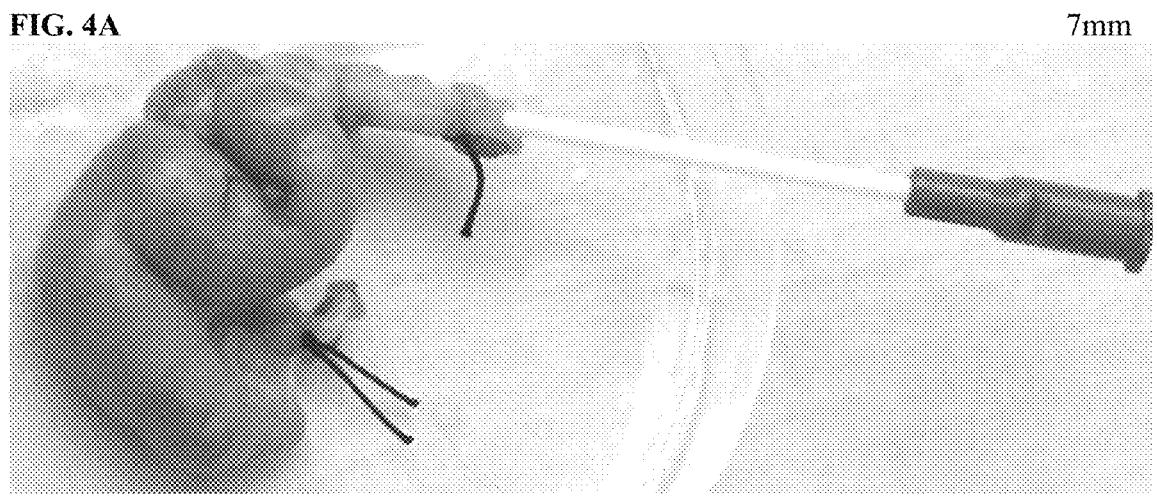
FIG. 4B 7mm
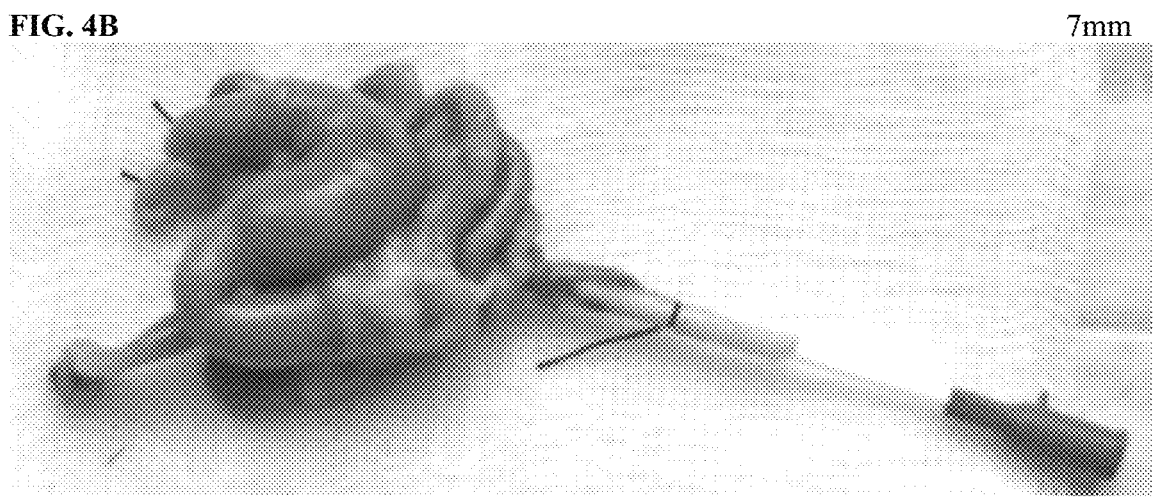

BIOMATERIAL FOR SUTURING

This invention refers to a material for suturing and its applications. More specifically, the invention refers to a material for suturing covered with cells that contribute in a biologically active way to the tissue repair process and therefore the healing of wounds.

BACKGROUND OF THE INVENTION

Any open wound poses the risk of infection and a channel for air and organic fluids to escape, making its closure an urgent necessity. In superficial skin wounds that do not pierce the dermis, spontaneous closure takes place when the edges of the wound come together, while in wounds where there is a clear separation of tissues only surgical action (suturing of the wound) can achieve this primary closure, also known as primary intention healing.

Traditionally, the suture has been the classical method for bringing the edges of the wound together in order to achieve the rapid tissue repair. Primary intention healing by suturing consists of bringing the edges of the wound together by introducing a suture in the tissues using a metal needle joined at one of its ends, passing the needle successively between both sides of the incision, thereby passively facilitating the closure of the wound.

Sutures are also used in surgical practice to stop bleeding (haemostasis) and to repair organs and other structures of the human body. In some situations, these sutures are particularly delicate due to the healing difficulties of the tissues they are used on. This is the case of sutures used for the colon wall, for tendons and in microsurgery involving nerve tissue and blood vessels.

One of the biggest disadvantages of sutures is the fact that the diameter of the needle is larger than that of the thread, so that the point where the needle is inserted is not taken up completely by the thread, thus generating areas where fluids can escape. This deficient closure of the wound is frequently the cause of post-operative complications, such as in the case of intestinal anastomosis in patients with carcinoma or diverticulosis who have had part of their intestine removed, after which the two healthy ends are joined together. In these patients, when the closure is incomplete faecal matter can leak into the surrounding tissues, which is a cause of peritonitis and places the patient's life at risk. This risk is higher in patients with thinner intestinal walls, as in the case of patients with intestinal inflammatory disease. In an attempt to avoid such passively leaking, biomedical adhesives are applied to the suture points to seal the opening caused when the needle is passed through the tissue.

The use of staples is an alternative to the classical suturing method. It enables the primary closure of the tissue to take place more rapidly, reduces the loss of blood, diminishes contamination and preserves blood flow. A limiting factor in the use of staples as a method of primary intention healing is the need to have access to the upper and lower part of the tissues being joined together. Furthermore, the force exerted when inserting the staples may cause the tissue to tear. One solution to this problem, in a new attempt at passive contention, i.e., without contributing in a biologically active way to improving the healing and tissue repair process, is to apply bioadhesives to the area where the staples are inserted.

These biocompatible adhesives work by facilitating the apposition of the tissues, providing a stable and regular biomechanical tension all along the incision, which helps to maintain tissue structure around the wound. They can be divided into two categories: biological adhesives, synthesized from plasmatic proteins; and synthetic polymers, primarily cyanoacrylate and its derivatives.

The biggest disadvantage of biological adhesives is the risk of viral transmission. Moreover, there are several disadvantages to the synthetic bioadhesives currently available. Most of them come in liquid form and are therefore difficult to apply, so they are used primarily on superficial wounds. They are also allergenic and potentially toxic substances. It has been described that these materials induce an inflammatory response in the body, which contributes to a delay in the regeneration and healing of the tissue, thus greatly limiting their usefulness (Aronson et al., 1970; Milde et al., 1989). Hence, a method which enables the wound to close and the suturing or tissues without inducing an inflammatory response, without the need to use this type of adhesives would be a particularly important advance as far as suturing internal tissue is concerned.

Sutures have now evolved to the point where there are sutures specifically designed for each type of operation. The surgeon chooses the type of suture based on the nature of the procedure, the characteristics of the patient, the pressure which the suture must support, etc. There is a wide variety of suturing thread available on the market today: absorbable, non-absorbable, monofilament and multifilament sutures, natural and synthetic, etc.

In order to improve the functional characteristics of sutures, there are diverse patents (GB577047, GB1401842, GB1430554, RU2125469) in which the threads are impregnated with germicide substances to prevent the sutures from being contaminated.

European patent EP0652017 protects biomaterials, the definition of which would include suturing materials, which have been coated to prevent blood constituents from adhering to the suture and thus delaying coagulation. The patent also describes the use of anticoagulants and substances with anti-inflammatory properties as the biomaterial coating.

U.S. Pat. No. 6,264,675 protects a suturing material composed of a suture coated with an adhesive material whose adhesive properties are activated when inserted into the tissue to be repaired, which is joined to a needle at one of its ends. The bioadhesive used in this type of intervention solves one of the main problems associated with suturing, since it prevents the loss of fluids through the needle insertion points. However, one of the disadvantages is the allergenic nature and potential toxicity of bioadhesives.

In addition, it is important to remember that all suturing materials induce "per se" an immunological response in the body, which recognises the foreign matter and which systematically delays the natural healing of the tissue. Therefore, concealing this foreign matter from the immunological system by coating it with autologous cells would be another particularly significant advance in the case of compromised sutures.

The suturing methods described above contribute passively to the apposition of the tissues without participating in a biologically active way in the tissue healing.

There are diverse cellular populations in adults which are known to be capable of contributing to connective tissue repair. Thus, for example, the stromal cells of bone marrow contain, among others, a population of cells known as mesenchymal stem cells (Friedenstein et al., 1976; Caplan et al., 1991; Pittenger et al., 1999). Studies conducted on these cells have demonstrated that there are different lineages of mesenchymal cells such as adipocytes (Beresford et al., 1972), chondrocytes (Johnstone et al., 1998), mioblasts (Wakitani et al., 1995), and osteoblasts (Haynesworth et al., 1992). Furthermore, multipotent stem cells which can be easily isolated have been identified (Zuk et al., 2001) in adipose tissue, which like bone marrow is derived from the embryonic mesoderm and is composed of a heterogeneous cell population. These cells are similar, though not identical, to the mesenchymal stem cells in bone marrow (De Ugarte et al., 2003) and can also be broken down into multiple mesenchymal cell lineages (chondrocytes, osteocytes, adipocytes, and mioblasts). Moreover, like the mesenchymal stem cells in bone marrow, they have neuron differentiating capacity (Zuk et al., 2002).

The ability to join biological tissues together has been one of the principal challenges of biomedical research. The ideal suture is that which is resistant and easy to handle, does not induce an inflammatory response by the tissue and does not foster infection. In other words, that which not only closes the wound but also contributes to full healing.

This invention refers to a suturing material that makes it possible to bring the ends of the tissue together thus facilitating healing and accelerating the repair process by contributing in a biologically active way to the formation of scar tissue. The use of such material also causes less inflammation of the sutured tissue which reduces the time required for the open wound to heal, minimizing the risk of infection and the loss of body fluids and consequently the number of surgical failures.

DESCRIPTION OF THE INVENTION

The biomaterial for suturing referred to in this invention is composed of a physiologically compatible material known as support material which is coated with a cellular population with proliferative and/or differentiation capacity, characteristics which are necessary to participate in the regeneration of the sutured tissue. Thus, this biomaterial for suturing is not limited to bringing the two ends of the open wound together, but also contributes actively to scar tissue formation, accelerating the tissue repair process. This innovation represents an important advantage, especially in the case of sutured internal organs and particularly for intestinal anastomosis as a result of resectioning the gastrointestinal tract or urogenital area.

A first aspect of the invention provides a biomaterial for suturing which is useful as a therapeutic agent in the treatment of wounds, both accidental and surgical, and in suturing tissues. This biomaterial is composed of a suturing support coated with a cellular population characterized by its proliferative and/or differentiation capacity.

In one preferred aspect, the support material for suturing includes but is not limited to staples, absorbable thread, non-absorbable thread, natural thread, synthetic thread, monofilament thread and multifilament thread (also called braids).

In another preferred aspect, the support material for suturing includes but is not limited to absorbable thread, non-absorbable thread, natural thread, synthetic thread, monofilament thread and multifilament thread or braids joined to a metal suturing needle.

In yet another preferred aspect, the support material for suturing is composed of absorbable synthetic monofilament thread joined to a metal suturing needle.

A second aspect of the invention refers to the use of cells with proliferative and/or differentiation capacity as the cellular population used to coat the biomaterial for suturing.

A preferred aspect refers to the use of stem cells as the cellular population used to coat the biomaterial for suturing.

A more preferred aspect refers to the use of pluripotent stem cells, capable of differentiating into any kind of tissue, as the cellular population used to coat the biomaterial for suturing.

A more preferred aspect refers to the use of multipotent stem cells, capable of differentiating any kind of tissue, as the cellular population used to coat the biomaterial for suturing.

An especially preferred aspect refers to the use of adult multipotent stem cells as the cellular population used to coat the biomaterial for suturing.

In one particular embodiment, the invention provides a biomaterial for suturing composed of a suturing thread joined to a metal needle at one end as the support material and adult multipotent stem cells as the cellular population used for coating.

In a preferred embodiment on of the invention, the adult multipotent stem cells capable of differentiating between cell types used as the coating population are isolated from human adipose tissue. In humans, the preferred source of adipose tissue is subdermal fatty tissue and the preferred collection method is liposuction.

Another aspect of the invention refers to the use of cellular populations of an autologous, alogenic or xenogenic nature, or a combination of these. The cellular population used for the coating will preferably be autologous cells.

An especially preferred aspect refers to the use of adult multipotent autologous stem cells isolated by liposuction as the cellular population for coating the suturing biomaterial of the invention (Example 1). The advantage of using adult autologous stem cells is that they are immunocompatible by nature and therefore do not cause inflammation problems or rejection. Furthermore, there are no legal or ethical impediments to using them. In a preferred execution of the invention, the biomaterial for suturing includes adult autologous stem cells as the coating material, their use being restricted to the patient from whom the cells are taken.

A third aspect of the invention includes the use of stem cells which have at least one characteristic of a specialized cell, as the cellular population used to coat the biomaterial for suturing to which the invention refers.

A preferred embodiment refers to the use of progenitor cells from a specialized cellular lineage obtained from the patient's stem cells which express at least one of the characteristics of the specialized progenitor cells as the cellular population used to coat the biomaterial for suturing to which the invention refers. This prevents the generation of inflammatory problems and rejection, as and the components of the suturing material would be concealed from the immunological system by coating it with autologous stem cells, which would undoubtedly improve the tissue repair process.

A preferred aspect refers to the use of stem cells that have been induced to differentiate in vitro into cells that express at least one of the characteristics of a specialized cell as the cellular population for coating the biomaterial for suturing.

A more preferred aspect refers to the use of multipotent stem cells which have been induced to differentiate in vitro to cells that express at least one of the characteristics of a specialized cell as the cellular population for coating the biomaterial for suturing. This includes but is not limited to the following cell types: epithelial cells, endothelial cells, adipocytes, myocytes, chondrocytes, osteocytes, neurons, astrocytes, oligodentrocytes, hepatocytes and pancreatic cells.

A fourth aspect of the invention refers to a biomaterial for suturing in which the cellular population for coating has been genetically modified.

A preferred embodiment refers to a biomaterial for suturing in which the cellular population for coating has been genetically modified to express factors that contribute to the tissue repair process, including but not limited to growth factors, morphogenetic factors, structural proteins and cytokines.

A fifth aspect of the invention refers to the biomaterial of the invention in which the cellular population for the coating is composed of a heterogeneous cellular population. A heterogeneous cellular population is defined as that which includes different types of cells or cells in different stages of differentiation or a combination of both.

A sixth aspect of the invention provides a method for obtaining the biomaterial for suturing of the invention in which the cellular population for coating is joined to the support material by adhesion.

A preferred aspect of the invention provides a method for obtaining a biomaterial for suturing in which the cellular population for the coating is joined to the support material by adhesion. This method involves:
1. expanding or propagating the cell population of choice;
2. submerging the suturing material in a suitable culturing medium for that cell population;
3. inoculating a suspension of the pre-cultivated cell population onto the suturing material;
4. cultivating the preparation under the right conditions, which includes but is not limited to dish cultures and dynamic cultures in tubes;
5. isolating the support material with an adequate cellular coating.

The expansion and growth stages of the cellular population used as a coating for the biomaterial support is known to those ordinarily skilled in the art.

A more preferred aspect of the invention provides a method for obtaining a biomaterial for suturing in which the support material has been previously coated with a material, the purpose of which is to improve the adhesion of the cell population. Said coating material of the support material includes but is not limited to peptides, antigens, proteins, antibodies, sugars and lipids. In an even more preferred aspect, said coating material would be extracellular matrix proteins from eukaryote cells or antibodies.

Another preferred aspect provides a method for obtaining the biomaterial for suturing which involves genetically modifying the cellular population of choice after expanding that cellular population.

An eighth aspect involves the use of the biomaterial for suturing of the invention in therapy.

A preferred aspect involves the use of the biomaterial for suturing to bring tissue edges together, which includes but is not limited to therapeutic applications in hemostasis, organ transplants, surgery of the gastrointestinal tract, surgery of the urogenital tract, surgery of the respiratory tract, eye surgery, vascular surgery, plastic and reconstructive surgery, surgery on muscle tissue, epithelial tissue, nerve tissues and the repair of tendons, osseous tissue and cartilaginous tissue.

A more preferred aspect of the invention refers to the use of the sutures coated with autologous stem cells in those cases where local inflammatory reaction generated by the suture could be harmful to the results of the surgical procedure.

An even more preferred aspect refers to the use of the biomaterial for suturing in bringing the edges of the tissue together in any surgical activities where an improvement to local scar formation capacity is desired.

An even more preferred aspect involves the use of the biomaterial for suturing to bring the edges of tissue together in intestinal anastomosis.

Another preferred aspect involves the use of the biomaterial for suturing to hold prostheses in place such as cardiac valves or neurosurgical valves.

Another aspect of the invention refers to the use of any prosthetic material (or device) used in medicine which is implanted in the human body and which frequently leads to biocompatibility problems, such as implant valves and surgical prostheses, which have been coated with cells.

DESCRIPTION OF THE FIGURES

FIG. 1 contains five panels, FIG. 1A-1E, showing a phase contrast photomicrograph, in visible mode, of the different fragments of suturing thread used as support material in Example 1.

FIG. 2 contains five panels, FIG. 2A-2E, showing a phase contrast photomicrograph, in ultraviolet mode, the degree of cellular coating achieved in the fragments of suturing thread used in example one after one week of incubation.

FIG. 3 contains two panels, FIG. 3A-3B, showing the general appearance of the abdominal cavity of rats after being laparotomized on the fourth post-operative date. A comparison of the general appearance (inflammation, general adhesions . . . ) enables us to differentiate two patterns in the evolution of scar tissue formation of the anastomotic suture.

FIG. 4 contains two panels, FIG. 4A-4B showing a photograph of a colic segment which contained the anastomosis once a catheter had been introduced at the proximal end, before determining the rupture pressure. FIG. 4A shows a photograph of the colic segment of one of the rats (no. 1) in group A (surgery performed using the biomaterial for suturing of the invention). FIG. 4B shows a photograph of the colic segment of one of the rats (no. 3) in group B (surgery performed with Vicryl® 4/0 thread). To compare the degree of inflammation of the resected colic segments shown in FIGS. 4A and 4B, we have used the length of a portion of the catheter as a reference, indicated by a black line drawn at the bottom of the figures and the real size of which is 7 mm.

DETAILED DESCRIPTION OF THE INVENTION

Figure 1A:
FIG. 1A shows the absorbable thread type vicryl (Ethicon) ref. V460.
Figure 1B:
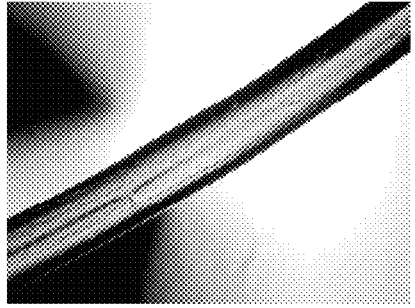
FIG. 1B shows the type of absorbable thread type monocryl (Ethicon) ref. Y3110.
Figure 1C:
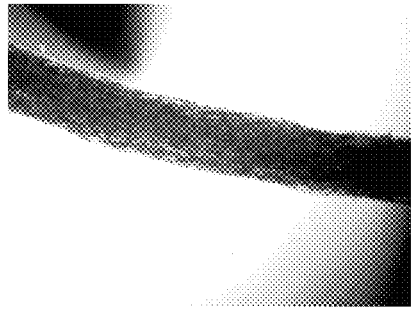
FIG. 1C shows the type of absorbable thread Dexon II (USS-DG) Ref. 9819-41.
Figure 1D:
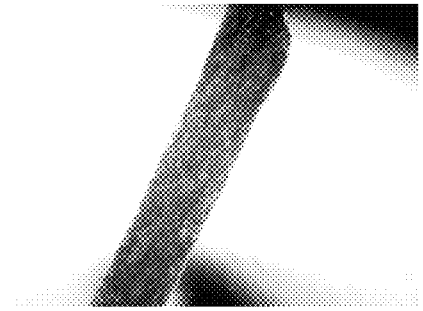
FIG. 1D shows the type of absorbable thread Safil quick (B/Braun) ref. 0046030
Figure 1E:
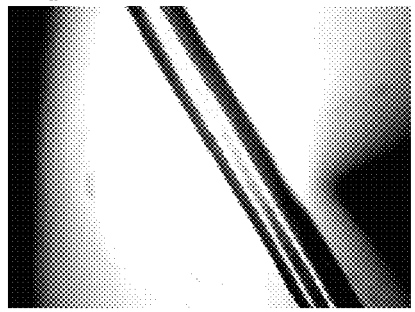
FIG. 1E shows the type of non-absorbable thread Ethilon (Ethicon) ref. W1621.
Figure 2A:
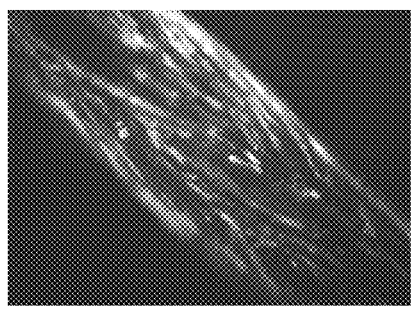
FIG. 2A shows the absorbable thread type vicryl (Ethicon) ref. V460.
Figure 2B:
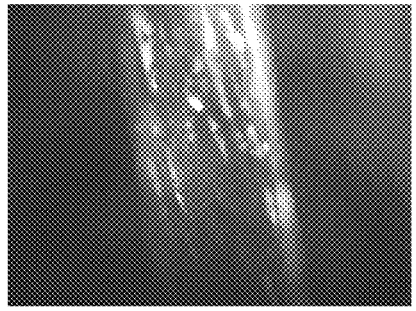
FIG. 2B shows the type of absorbable thread type monocryl (Ethicon) ref. Y3110.
Figure 2C:
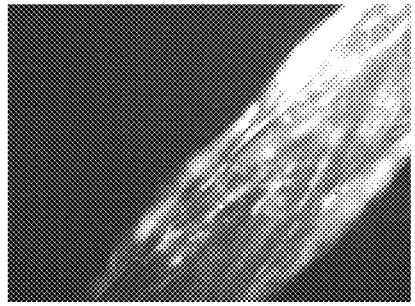
FIG. 2C shows the type of absorbable thread Dexon II (USS-DG) Ref. 9819-41.
Figure 2D:
FIG. 2D shows the type of absorbable thread Safil quick (B/Braun) ref. 0046030
Figure 2E:
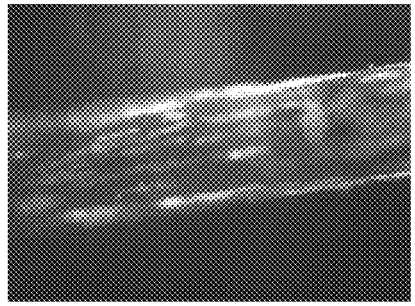
FIG. 2E shows the type of non-absorbable thread Ethilon (Ethicon) ref. W1621.
Figure 3A:
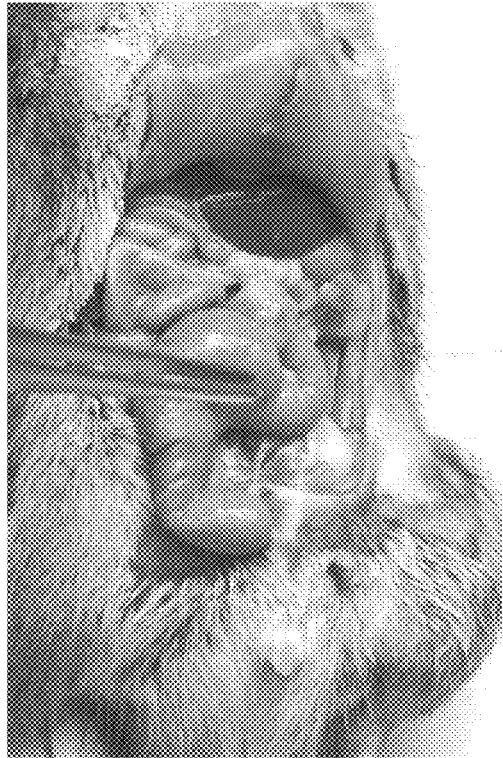
FIG. 3A shows a photograph of one of the rats (no. 1) in group A (surgery performed with the biomaterial for suturing of the invention).
Figure 3B:
FIG. 3B shows a photograph of one of the rats (no. 3) in group B (surgery performed with Vicryl® 4/0 thread)

The invention provides a biomaterial for suturing comprising a support material for suturing, preferably a suturing thread, and a cellular population covering the support material. The cellular population used for coating is characterized by its proliferative and/or differentiation capacity.

In one particular execution, the invention provides a biomaterial for suturing composed of a suturing thread joined to a metal needle at one of the ends as the support material and adult autologous stem cells obtained by liposuction for the cellular population.

The following examples are given to illustrate but do not limit this invention.

EXAMPLE 1

Suturing Threads Coated with Adult Human Stem Cells from Adipose Tissue

The object of this experiment was to study the capacity of a certain type of cell to adhere to different types of suturing threads acting as the support material for the biomaterial for suturing of this invention.

1.1. Materials

Five different types of suturing thread, all of the same thickness 3-0 (2 Ph.Eur.) were used, all synthetic (Table 1).

Adherent adult human lipo-derived stem cells (LDSC) were used as the cellular population for coating, after first being transduced with retrovial vectors that code for Cop-GFP, green fluorescent protein, used as a gene marker.

1.1.1. Isolation of LDSC

The adipose tissue was obtained by liposuction. A cannula with a blunt end was introduced into the subcutaneous space through a small periumbilical incision (less than 0.5 cm in diameter). The suction was performed by moving the cannula along the adipose tissue compartment located under the abdominal wall, thus aiding the mechanical disruption of the adipose tissue. To minimize the loss of blood, a saline and epinephrine solution was injected as a vasoconstriction agent. 80-100 ml of raw lipoaspirate cells were obtained from each patient using this procedure.

The lipoaspirate was then washed with a phosphate and saline solution (PBS). The adipose tissue was then disrupted by digestion of the extracellular matrix with type II collagenase in saline solution (5 mg/ml) at 37° for 30 minutes to release the cellular fraction. The collagenase was inactivated by adding an equivalent volume of DMEM medium with 10% fetal bovine serum. The cellular suspension was centrifuged at 250 g for 10 minutes to obtain a cell deposit. The cells were resuspended in DMEM medium with 10% fetal bovine serum. NH4Cl was added at a final concentration of 0.16M and the cell; incubated for 10 minutes at room temperature to induce the lysis of erythrocytes present. The suspension was centrifuged at 250-400 g and resuspended in DMEM-10% FBS with 1% ampicillin-streptomycin. Finally, the cells were inoculated at a rate of 20-30,000 cells per cm2 onto dishes.

1.1.2. Culturing of LDSCs

The cells were kept in culture for 20-24 hours at 37° in an atmosphere with 5% CO2. After 24 hours of incubation, the dishes were washed with PBS to eliminate the cells that had not adhered and cellular remains.

1.1.3. Transfection of Adherent LDSCs with Cop-GFP Gene Marker

Transfection of the LDSCs which showed adherence characteristics by means of transduction with supernatant containing retroviral particles, RetroFect®, pseudotyped with VSV-G (vesicular stomatitis virus glycoprotein) which code the Cop-GFP gene marker. Cop-GFP is a copepod green fluorescent protein (pontellina plumata) which makes it easy to identify and select the cells infected by direct fluorescence. The fluorescent protein does not enter the cellular nucleus. This is an advantage since the cells that are expressing the Cop-GFP protein can be easily distinguished from interfering fluorescent particles.

The method used in the transduction of the adherent LDSCs consisted of:
1. Adding polybrene (contributor to retroviral transduction) to the retroviral supernatant at a final concentration of 8 µg/ml of polybrene.
2. The medium of the target cells was changed and replaced by retroviral particles using approximately 106 µl of retroviral supernatant (including additives) per $cm^2$ of surface.
3. A dynamic transduction method was used to infect the cells. The cells were centrifuged at 1000 g for 60 minutes at 37° C. in the presence of retroviral supernatant.
4. The supernatant was removed and a fresh culturing medium of complete DMEM was added (DMEM-10% FSB with 1% ampicillin-streptomycin). The transduced cells were cultured for 48-72 hours in the culturing medium.
5. The cells were removed from the culture dishes with a mixture of tripsine-EDTA.
6. A proportional part was analysed by flow cytometry; the rest of the cells were transferred to another culturing container for expansion.

1.2. Test of the Adhesion of Cells to the Suturing Threads

Five different types of suturing threads were selected for testing as support material. Fragments measuring approximately 1 cm long were cut, introducing 2 thread fragments per bowl, on culturing dishes with 24 bowls.
1. 0.5 ml of the complete culturing medium was added to each one of the bowls to moisten the thread and to see if the threads would stay submerged in the culturing medium or if they would float. The tested threads either did not float or when forced under the medium they remained at the bottom of the bowl.
2. A suspension of LDSC cells was prepared in a concentration of 50,000 cells/ml and 1 ml of this suspension was added to each bowl.
3. The culturing dishes onto which the threads were deposited were cultured in the presence of the cellular suspension in an atmosphere with 5% $CO_2$ at 37° C. for 20-24 hours.
4. The degree of cellular coating of the threads achieved after 20-24 hours of incubation was observed under the microscope, in visible mode and fluorescent mode.
   In visible mode, it was not possible to detect the cells on the thread although we did detect the presence of very disperse cells at the bottom of the bowl. However, in fluorescent mode, thanks to the expression of the Cop-GFP in the transfected LDSC cells, some individual fluorescent cells were observed on the threads, although very few in number.
5. The degree of cellular coating of the threads achieved after 48 hours of incubation was observed under the microscope in visible mode and fluorescent mode. No significant changes were observed in the coverage of the threads compared to 24 hours of incubation. The threads were moved to bowls with a new culturing medium.

Starting at this time, the culturing medium was changed every 2-3 days according to the calendar.

6. The degree of cellular coating of the threads achieved after 72 hours of incubation was observed under the microscope in visible mode and fluorescent mode. Groups of cells on some of the tested threads were observed and photographed. It was even possible to differentiate different cells by their nuclei, since Cop-GFP is not expressed in the cell's nucleus.

7. After one week of incubating the transduced LDSC cells with Cop-GFP in the presence of the threads, an increase in the degree of cellular coverage of the surface of the threads was observed, thanks to the cells generated by the division of the cell which initially adhered to the threads.

EXAMPLE 2

Use of the Biomaterial for Suturing for Intestinal Anastomosis

The object of this test was to determine the characteristics of the biomaterial for suturing provided by this invention and the advantages it offers compared to conventional sutures by performing colical anastomosis in rats.

After performing the anastomosis with the biomaterial for suturing of the invention and simultaneously with non-cell-coated threads used as a negative control, a series of parameters were determined to evaluate the status of the anastomotic lesion and compare the results obtained with both types of thread.

2.1. Surgical Procedure 2.1.1. Animals and Suturing Material 12 adult BDIX rats with weights ranging between 130-260 grams were used in the experiment. Two to obtain the stem cells from the 4 rats from the subdermal adipose tissue and ten to study the colic sutures. The cell-coated threads were prepared following a protocol similar to that illustrated in example 1. The BDIX rats are syngenic which means that they are genetically identical and immunologically compatible. Each rat was identified by a number from 1 to 10 and each one was assigned a batch of sutures with the same number.

The sample was divided into two groups depending on the suturing material used for the anastomosis:

Group A (5 rats): Simple colic anastomosis performed with the biomaterial for suturing of the invention. More specifically, Vicryl® (polyglactin 910) 4/0 threads were used, an absorbable braided suture, coated with cells derived from the adipose tissues of BDIX rats. The same protocol as described in Example 1 was used to prepare the biomaterial for suturing.

Group B (5 rats): Considered the control group. Simple colic anastomosis performed with Vicryl® (polyglactin 910) 4/0 threads.

50% of the suture batches were cultured in the presence of stem cells (biomaterial for suturing of the invention) and the other half were incubated, in identical conditions, in the presence of the culturing medium only. Therefore, it was impossible to differentiate the two types of suturing used by their appearance. This was a blind study since the surgeons did not know which type of thread was used in each surgical procedure.

2.1.2. Simple Colic Anastomosis

The rats were lap arotomized under general anaesthesia after 24 hours of fasting with "ad libitum" water. The colon was completely sectioned at the mid-point of the transversal colon, taking care not to damage the margin vascularization and to prevent haemorrhaging. The single layer everted anastomosis was then performed with 3 stitches. Each stitch was tied three times. When the anastomosis was complete, the colon was put back into the abdominal cavity and the laparotomy closed with 0 silk thread on two planes.

2.2. Evaluation of Healing

The animals were sacrificed by decapitation on the fourth day after surgery. With the animal in asystole, the abdomen was opened to evaluate the dehiscence, dilation, obstruction, general adhesions, difficulty in separating general adhesions and determination of adhered structures.

Evaluation criteria of the variables under study:

1. Clinical dehiscence (De): Existence of free colic content in the peritoneal cavity.
2. Dilation (Di): Considered positive when the diameter of the pre-anastomotic transversal colon was at least two times larger than the diameter of the post-anastomotic transversal colon.
3. Obstruction (Ob): Absence of foetal content in the distal colon to the anastomosis.
4. General adhesions (GA): Measurements were taken based on a qualitative evaluation scale of the number of adhesions in the peritoneal cavity (Ellis H., 1962; Verreet P R et al, 1992). Four levels or degrees were established: 0=no adhesions; 1=very localized adhesions; 2=local-regional adhesions; 3=diffuse adhesions.
5. Separation of the general adhesions (Se). Lysis by traction: Three levels were established: 1=easy, i.e., most of the adhesions could be separate with gentle traction; 2=moderate, most of the adhesions could be separate with a blunt instrument; 3=difficult, most of the adhesions required a sharp instrument to be separated.
6. Adhered structures (AS): Evaluation of which anatomical structures had adhered to the anastomotic circumference. 4 categories were established: 1=omentum, 2=small intestine, 3=colon, 4=other locations.

The measurement of resistance to intraluminal pressure can be expressed as the rupture pressure, i.e., the pressure at which an anastomosis subject to growing intraluminal pressure is disrupted or as the rupture tension which expresses the circular tension to which the wall is subjected at the time of the rupture.

2.2.1. Measurement of Rupture Pressure (RP)

Using an infusion pump connected to a pressure-measuring system it is possible to determine the pressure at which a leak can occur through the anastomotic line (rupture pressure).

After drying a colic segment containing the anastomosis, the distal end was closed with a 1/0 silk suture. The proximal end was similarly closed after introducing an intravenous perfusion catheter. The catheter is connected to a three-stage valve or "T" system in which one of the lines goes to the capsule of a pressure transducer that registers the pressure variations and sends the signals to a digital polygraph system. The data are then sent to a computer for analysis and storage.

The other line is connect to a perfusion pump filled with physiological solution tinted with methylene blue to observe the time and place of the rupture.

2.2.2. Rupture Tension of the Wall (RT)

The rupture tension is determined by measuring the anastomotic circumference after setting the piece in 20% formol for four days. A lengthwise cut was made with a scalpel in the colon segment containing the anastomosis. With a graduated rule, the internal circumference (cn) of the piece was measured in tenths of a millimetre. Knowing the length of the internal circumference allows us to calculate the internal colon radius (r) applying the following formula:

$$cn = 2\pi r.$$

The rupture tension (RT) is a function of the rupture pressure (RP) and the internal colon radius (r) according to the Laplace Law. It is obtained by applying the following formula:

$$RT = 1.33 \times 10^3 \times RP \times r \ (RT = \text{dinas/cm}; \ RP = \text{mmHg}; \ r = \text{cm})$$

2.3. Results

Colic anastomosis was performed on 10 adult BDIX broken down into two groups, A and B, according to the suturing material used. Two of the animals used to evaluate the healing of the anastomosis, one from each group, had to be excluded from the study. During the surgery, one of the animals suffered a torn mesosigmoid while in another animal the anastomosis was torn when introducing the catheter in the distal end of the colic when measuring the rupture pressure.

Table 2 shows the results obtained for the different variable analysed in the evaluation of the anastomotic suture.

2.4. Discussion

The healing of the anastomotic wound was evaluated on the fourth day after surgery, as this is considered the most critical day in the evolution of colic anastomosis (Ravo, 1988).

After opening the abdominal cavity, the quadrants were pulled back to expose the entire peritoneal cavity. Surprisingly, an assessment of the general appearance (inflammation, general adhesions) was sufficient to differentiate two different patterns in the evolution of the healing of the anastomotic suture. The animals on which conventional suturing thread had been used (Group B) presented a higher level of general inflammation and a higher number of structures adhered to the intestine than the animals which had been operated on using the biomaterial for suturing of the invention (Group A).

First of all, it was determined that the handling of the biomaterial for suturing of the invention is identical to that of conventional thread. The presence of cells coating the threads does not alter the manageability of the sutures.

A series of variables was determined to evaluate the healing of the anastomotic suture:

1. Dehiscence: No faecal matter was observed in the peritoneal cavity in either one of the groups. The surgical techniques and the suturing material used were appropriate for the type of rat in question.
2. Dilation: Dilation of the pre-anastomotic colon was observed in 75% of the cases in both groups.
3. Obstruction: While the dilation of the pre-anastomotic segment was similar in both groups, the clinical repercussion was different. 100% of the animals in the group treated surgically with the biomaterial of the invention (Group A) showed no intestinal obstruction, while obstruction was observed in 50% of the animals treated with conventional sutures (Group B). The absence of colic obstruction implies a series of clinical advantages in terms of the speed of the patient's recovery and the reduction of post-operative complications.
4. General Adhesions: A qualitative assessment of the number of adhesions on the peritoneal cavity revealed that in Group A 75% of the cases showed local-regional adhesions, while in Group B 75% of the cases showed diffuse adhesions.
5. Separation of adhesions: In Group A 75% of the cases pertained to Level 1 or adhesions which are easily separated. Only one case (25%) was classified as Level 3, requiring the use of a sharp instrument for separation. However, this animal's cecum had been inverted during the surgical procedure. On the contrary, 100% of the cases in Group B pertained to Level 3.
6. Adhered structures: In group A, the epiploon is adhered in 75% of the cases and 100% of the cases showed adhesions to two different structures. In Group B, 100% of the animals had adhesions to the epiploon and small intestine. In 75% of the cases adhesions to 3 different structures were observed and in the remaining case there were adhesions to 4 different structures.

The adhesions are pathologically important since they alter the normal physiology of serous surfaces. Surprisingly, the animals in Group A showed a more regional pattern of adhesions which were easier to separate and a lower number of adhered structures, which implies a reduction of the complications caused by intraperitoneal adhesions: intestinal obstruction, chronic abdominal pain and infertility. The use of a foreign matter in the abdominal cavity produces a high level of adhesions (Ellis H, 1962, Zarapico et al, 1972). The decrease in the adhesions observed in the trial could have been due to the fact that the biomaterial of the invention is not recognized as something foreign by the body.

The purposes of using a physical method for evaluating the healing of the anastomosis are to ensure that it is as comprehensive as possible, since the use of other methods, such as biochemical or histological, give us only a partial view of these processes at the anastomosis level.

Figure 5:
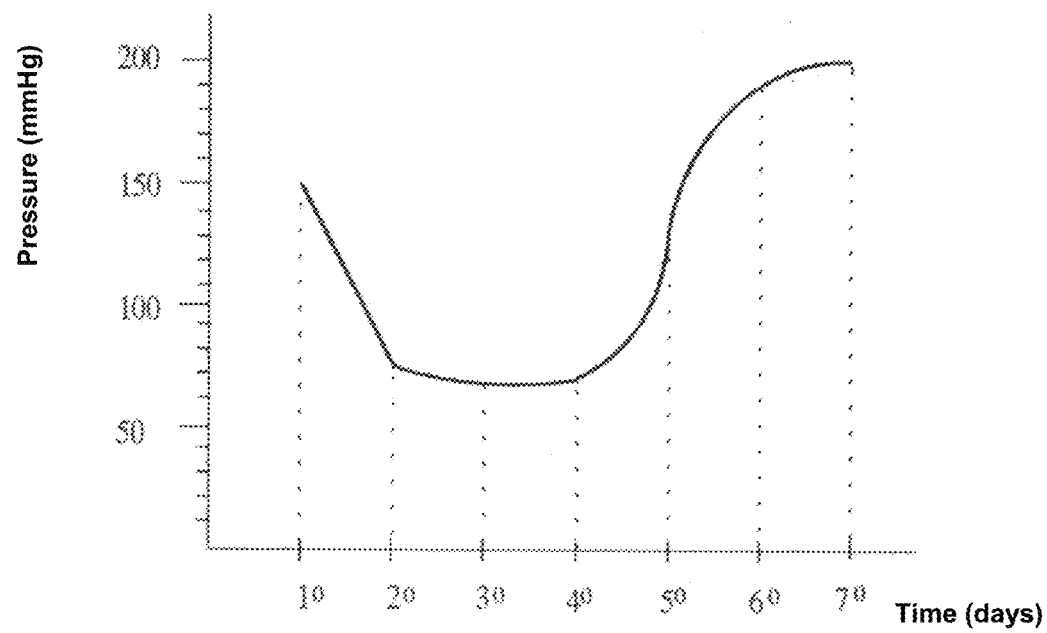
FIG. 5 shows a diagram that illustrates the variation in the physical resistance of a colic suture in the presence of increased intraluminal pressures, depending on how much time has elapsed. Hence, it has been observed that within the first few hours after surgery there is a decline in the resistance, the lowest levels being detected between the third and fourth days after surgery.

The physical resistance of a colic suture to increased intraluminal pressure varies depending on the time which has elapsed. Hence it was observed that in the first few hours following the surgery there is a drop in resistance, the lowest values being detected between the third and fourth days following surgery. At that time, there is a rapid increase in resistance which continues to mount until on the seventh day after surgery the values are close to those of the resistance of the colic wall in its physiological state (FIG. 5). This inflection in the curve of the anastomotic force around the fourth day after surgery is closely linked to the cellular and chemical processes that take place during the inflammatory and repair processes.

In Group A, the average resistance of the anastomosis, calculated as the rupture pressure, is 46.1575 mmHg, which is higher than the average resistance observed in Group B: 47.7325 mmHg.

The disadvantage of measuring the resistance to intraluminal pressure by determining the rupture pressure is that it does not take the diameter of that colon segment into account. If we measure the rupture pressure without taking the diameter of the colon segment into account, we set the Laplace Law aside ($T = P \times r$) and we do not consider the fact that for the same rupture pressure the tension which the wall supports is greatest in the area with the largest radius (Asencio F. et al, 1989).

When calculating the average rupture tension, we saw that in Group A the intestinal wall supports an average rupture tension of 181.122 dinas/cm, which is higher than the average resistance found in Group B: 1631.57 dinas/cm.

Therefore, while the differences as far as rupture pressure are not statistically significant, the calculation of rupture tension corroborated the results obtained: the suture using the biomaterial of the invention showed greater resistance to pressure than the suture using conventional thread. Furthermore, the maximum rupture resistance value was seen in one of the animals in Group A and the lowest value was observed in Group B. The higher resistance to rupture of the anastomotic suture implies a lower risk of dehiscence, separation of part of the anastomosis, which is a serious complication and one of the leading causes of post-operative death in colic surgery.

REFERENCES

Aronson S B, McMaster P R, Moore T E Jr, Coon M A. Toxicity of the cyanoacrylates. Arch Opthalmol. 1970 September; 8(3)342-9.
Asencio Arana F, Martinez Soriano F, Fenollosa Vazquez R. Aproximacion a los estudios de los anastomosis intestinales experimentales. Metodos bioquimicos, fisicos y microangiográficos. Cir Esp 1989; 46:805-810.
Beresford J N, Bennett J H, Devlin C, Leboy P S, Owen M E. Evidence for an inverse relationship between the differentiation of adipocytic and osteogenic cells in rat marrow stromal cell cultures. J. Cell Sci. 1992 June; 102(Pt 2): 341-51.
Caplan Al. Mesenchymal stem cells. J Orthop Res. 1991 September; 9(5)641-50.
De Ugarte D A, Morizono K, Elbarbary A, Alfonso Z, Zuk P A, Zhu M, Dragoo J L, Ashjian P, Thomas B, Benhaim P, Chen I, Fraser J, Hedrick M H. Comparison of multi-lineage cells from human adipose tissue and bone marrow. Cells Tissues Organs. 2003; 174(3)101-9.
Ellis, H. the aetiology of postoperative abdominal adhesions. An experimental study. Br J Surg 1962; 50:10-16.
Friedenstein A J. Precursor cells of mechanocytes. Int Rev Cytol. 1976; 47:327-59.
Haynesworth SbE, Goshima J, Golberg V M, Caplan A I. Characterization of cells with osteogenic potential from human marrow. Bone. 1992; 13(1)81-8.
Johnstone B, Hering T M, Caplan A I, Goldberg V M, Yoo J U. In vitro chondrogenesis of bone marrow-derived mesenchymal progenitor cells. Exp Cell Res. 1998 Jan. 10; 238(1)265-72.
Milde L N. An anaphylactic reaction to fibrin glue. Anesth Analg. 1989 November; 69(5)684-6.
Pittenger M F, Mackay A M, Beck S C, Jaiswal R K, Douglas R, Mosca J D, Moorman M A, Simonette D W, Craig S, Marshak D R. Multilineage potential of adult human mesenchymal stem cells. Science. 1999 Apr. 2; 284(5411)143-7.
Ravo B: Colorectal anastomotic healing and introcolonoic bypass procedure. Surg Clin North Am 1988; 68:1267-1294.
Verreet P R, Fakir C, Ohmann C, Roer H D. Preventing recurrent postoperative adhesions: An experimental study in rats. Eur Sug Res 1992; 21:267-273.
Wakitani S, Saito T, Caplan A I. Myogenic cells derived from rat bone marrow mesenchymal stem cells exposed to 5-azacytidine. Muscle Nerve. 1995 December; 18(12) 1417-26.
Zarapico Romero M, Saez López de Rueda F. La asociaciOn fibrino-desoxirribonucleasa en la profilaxis de la adherencias peritoneales post-operativas. Rev Fac Med Sevilla 1972; 20:347-362.
Zuk P A, Zhu M, Ashjian P, De Ugarte D A, Huang J I, Mizuno H, Alfonso Z C, Fraser J K, Benhaim P, Hedrick M H. Human adipose tissue is a source of multipotent stem cells. Mol Biol Cell. 2002 December; 13(12)4279-95.
Zuk P A, Zhu M, Mizuno H, Huang J, Futrell J W, Katz A J, Benhaim P, Lorenz H P, Hedrick M H. Multilineage cells from human adipose tissue: implications for cell-based therapies. Tissue Eng. 2001 April; 7(2)211-28.

TABLE I

| No. Name | Type | Mark | Reference |
|---|---|---|---|
| 1. VICRYL | Polyglactin 910. Braiding. Violet. Absorbable suture | ETHICON | V460 |
| 2. DEXON II | Polyglycolic Acid Braiding. Green. Absorbable suture | USS-DG | 9819-41 |
| 3. MONOCRYL | Polyglecaprone 25. Monofilament. Violet. Absorbable suture | ETHICON | Y3110 |
| 4. SAFILQUICK | Polyglycolic Acid Braiding. White. Absorbable suture | B-BRAUN | 0046030 |
| 5. ETHILON | Polyamide 6 Monofilament. Blue. Non-absorbable suture | ETHICON | W1621 |

TABLE II

| | INFLAMMATION | | | ADHESIONS | | | RESISTANCE | | |
|---|---|---|---|---|---|---|---|---|---|
| ANIMAL | De | Di | Ob | GA | Se | AS | RP (mmHg) | r (cm) | RT (dinas/cm) |
| 1 | NO | NO | NO | 2 | 1 | 1, 3 | 43.1 | 0.038 | 2178.27 |
| 4 | NO | YES | NO | 2 | 1 | 1, 2 | 41.73 | 0.035 | 1942.53 |
| 6 | NO | YES | NO | 2 | 1 | 2, 4 | 63.1 | 0.022 | 1846.2 |
| 7[a] | NO | YES | NO | 3 | 3 | 1, 2 | 36.7 | 0.027 | 1317.89 |
| AVG | | | | | | | 46.1575 | | 1821.22 |
| 2 | NO | YES | YES | 3 | 3 | 1, 2, 3, 4 | 52 | 0.024 | 1646 |
| 3 | NO | YES | NO | 2 | 3 | 1, 2, 3 | 50.47 | 0.035 | 2349.38 |
| 5[b] | NO | NO | NO | 3 | 3 | 1, 2, 3 | 52.06 | 0.025 | 1758.69 |
| 10 | NO | YES | YES | 3 | 3 | 1, 2, 4 | 24.4 | 0.024 | 772.23 |
| AVG | | | | | | | 44.7325 | | 1631.575 |

TABLE II-continued

| | INFLAMMATION | | | ADHESIONS | | | RESISTANCE | | |
|---|---|---|---|---|---|---|---|---|---|
| ANIMAL | De | Di | Ob | GA | Se | AS | RP (mmHg) | r (cm) | RT (dinas/cm) |
| Group A: 1, 4, 6, 7<br>Group B: 2, 3, 5, 10 | | | | | | $T_{student}$ | 0.878536971 | | 0.62896192 |

COMMENTS:
[a] blind inverted
[b] 7 stitches

Abbreviations:
Clinical dehiscence (De)
Dilation (Di)
Obstruction (Ob)
General adhesions (GA)
Separation of general adhesions (Se)
Adhered structures (AS)
Rupture pressure (RP)
Radius (r)
Rupture tension (RT)

The invention claimed is:

1. A method of suturing gastrointestinal tissue, comprising the steps of:
   (a) isolating stem cells from adipose tissue of a subject, thereby obtaining adipose derived stem cells;
   (b) adhering the adipose derived stem cells to a thread such that the adipose derived stem cells coat the thread; and
   (c) bringing edges of tissue together using the thread by introducing the thread in the tissues using a metal needle and passing the needle successively between the edges of the tissue.

2. The method of claim 1, wherein the adipose derived stem cells are allogeneic adipose derived stem cells.

3. The method of claim 1, wherein the adipose derived stem cells are obtained by liposuction.

4. The method of claim 1, wherein the thread is a monofilament or multifilament thread.

5. The method of claim 1, wherein the thread is absorbable.

6. The method of claim 1, wherein the thread is made of a natural material.

* * * * *

UNITED STATES PATENT AND TRADEMARK OFFICE
CERTIFICATE OF CORRECTION

PATENT NO. : 11,253,632 B2
APPLICATION NO. : 16/436578
DATED : February 22, 2022
INVENTOR(S) : Damian Garcia Olmo et al.

It is certified that error appears in the above-identified patent and that said Letters Patent is hereby corrected as shown below:

On the Title Page

Please delete:
"This patent is subject to a terminal disclaimer"

Signed and Sealed this
Thirty-first Day of January, 2023

Katherine Kelly Vidal
*Director of the United States Patent and Trademark Office*